United States Patent
Zamfes

(10) Patent No.: US 7,430,931 B2
(45) Date of Patent: Oct. 7, 2008

(54) MICROGRANULOMETRY AND METHODS OF APPLICATIONS

(76) Inventor: Konstandinos Zamfes, 1830 - 10 Ave S.W., Calgary (CA) T3C 0J8

( * ) Notice: Subject to any disclaimer, the term of this patent is extended or adjusted under 35 U.S.C. 154(b) by 0 days.

(21) Appl. No.: 10/710,840

(22) Filed: Aug. 5, 2004

(65) Prior Publication Data
US 2005/0087018 A1    Apr. 28, 2005

Related U.S. Application Data

(60) Provisional application No. 60/481,197, filed on Aug. 8, 2003.

(51) Int. Cl.
*G01N 15/00* (2006.01)
(52) U.S. Cl. .................................. 73/865.5
(58) Field of Classification Search ............... 73/38, 73/865.5, 53.01–64.56
See application file for complete search history.

(56) References Cited

U.S. PATENT DOCUMENTS

| | | | | |
|---|---|---|---|---|
| 2,498,198 | A | * | 2/1950 | Beeson ........................ 73/38 |
| 2,699,673 | A | * | 1/1955 | William ..................... 73/61.65 |
| 3,427,886 | A | * | 2/1969 | Haas ......................... 73/865.5 |
| 3,519,353 | A | * | 7/1970 | Gonshor et al. ............. 356/335 |
| 3,788,146 | A | * | 1/1974 | Hartman ..................... 73/865.5 |
| 3,943,754 | A | * | 3/1976 | Orr, Jr. ....................... 73/61.63 |
| 4,205,384 | A | | 5/1980 | Merz |
| 4,929,079 | A | | 5/1990 | Delfour |
| 5,095,451 | A | * | 3/1992 | Allen ........................... 702/29 |
| 5,359,906 | A | * | 11/1994 | Kanai ......................... 73/865.5 |
| 6,301,953 | B1 | | 10/2001 | Zamfes |
| 6,386,026 | B1 | | 5/2002 | Zamfes |

* cited by examiner

Primary Examiner—Hezron E. Williams
Assistant Examiner—John Fitzgerald
(74) Attorney, Agent, or Firm—Diederiks & Whitelaw, PLC

(57) ABSTRACT

An apparatus and process for measuring the granulometry separations in discrete media and unconsolidated sediments for relatively small sample quantities (5 cc containers of drilling cuffings) is disclosed. A small diameter glass tube may be filled with a small amount of sample, and water added. After shaking and placing it vertically, the larger, denser particles will settle near the bottom. Particle size will tend to decrease in size towards the top. Placing the tube near an array of sensors may perform a quantitative analysis such as sonic, gamma and optical sensing. One or more sensors are slowly moved past the tube and digitized readings be recorded. The collected readings are interpreted by the quantity and sizes of particles and by their distribution. The results may be presented in various ways and used to calculate the environmental index of energy of accumulation and to quantify the relative permeability of a potential reservoir.

20 Claims, 7 Drawing Sheets

US 7,430,931 B2

MICROGRANULOMETRY AND METHODS OF APPLICATIONS

CROSS REFERENCE TO RELATED APPLICATIONS

U.S. Pat. No. 4,929,079 May, 1990 Delfour, et al. 356/336; U.S. Pat. No. 4,205,384 May, 1980 Merz, et al. 702/29 U.S. Pat. No. 6,301,953 October 2001 Zamfes, at al. 73/38; U.S. Pat. No. 6,386,026 May 2002 Zamfes at al. 73/152.04.

BACKGROUND OF INVENTION

During oil and gas exploration conventional granulometry analysis is a time consuming, logistically complex procedure. It requires the transportation and storage of a large number of samples of the rock cuttings produced during drilling to the laboratory. Conventional practice is to have a field worker manually scoop a shovel full of the cuttings as they fall off of the shaker table (the part of the drilling rig which separates the rock cuttings from the drilling fluid so that the fluid can be reused). The sample shovel-full is poured into a canvas bag and transported from the well site (which is typically remotely located) to a laboratory. Conventionally, a series of tall, wide cylindrical containers are used to separate the cuttings by particle size and density. The sample is combined with water and poured into a container. At a predetermined interval the upper portion of the partially settled sample is siphoned off and allowed to settle in a second container. This procedure is repeated until the size of particle remaining in suspension is of a desired size. Next, all the containers are dried and weighed using an analytic balance. The quantity of specific grain sizes is tabulated for interpretation. It is impractical to perform conventional granularity analysis during modern high speed drilling. Consequently, various down hole logging tools are used in place of conventional granulometry analysis to assess Porosity and Permeability.

Exploration focuses on the productivity of a potential reservoir during the drilling of a well in an unconsolidated formation. Detailed rock sampling and a corresponding granulometry analysis are the most accurate and direct method for defining the potential production horizons. Granulometry properties provide the best information for estimating the Porosity and Permeability of a reservoir. Unfortunately, conventional granulometry is not used in the exploration of unconsolidated formations due to the logistical problems associated with it. Instead, Logging properties (which are determined using down-hole tools) are substituted for granulometry parameters when calculating Porosity and Permeability. This produces less accurate information about a potential production zone.

In the proposed Microgranulometry, the apparatus and the process solve all the problems of conventional granulometry and produce useful, accurate information. Microgranulometry produces direct quantitative measurements of the SHALE, SILT and SAND content of the formation sample.

SUMMARY OF INVENTION

The proposed micro granulometry apparatus and process is capable of producing detailed results with a very small amount of cuttings. The micro sample is placed in micro tube 1 FIG. 1 and water is added. Then the aggregate is shaken and placed vertically in the Microgranulometry apparatus FIG. 3 for further analyses. The micro tube can be passed along one or more sensors 10, 11, 12, 13 and the results are recorded on a computer.

A microscopic analysis is performed by placing the micro tube 1 in front of the Horizontal microscope disclosed in U.S. Patent Provisional Application No. 60/481,408, EFS ID 48139, Horizontal Binocular Microscope for vertically gravitated and floating samples. This process will allow a technician to visually distinguish the horizontal borders of Sand at the bottom, Silt in the middle and Shale/Clays on the top. In some cases the colloidal substance or hydrocarbons maybe visually distinguished. A Measuring Scale is used to measure the vertical length of each substance in millimeters from the bottom of the test tube once the layers are defined. For example if the total sample placed in the tube, in dry condition is 50 mm and the Sand is 35 mm. The Silt is 5 mm. and the Shale is 10 mm, then the ratio is calculated as 35/50, 5/50, 10/50.

Also the results produced may be used in calculating the Environmental Index (pertaining to the energy of accumulation) and to the quantification of the Relative Permeability disclosed by the author in U.S. Pat. No. 6,301,953 B1, Date Oct. 16, 2001, Quantification of drilling mud cuttings characteristics as a measure of relative permeability.

After the analyses the micro tube 1 may be stored for further review.

BRIEF DESCRIPTION OF DRAWINGS

In FIG. 2 the pebbles 7 are at the bottom. A sequence of gravitationally separated particles in liquid media (from course to very fine) can also be seen in FIG. 2. These layers are: pebble 7, sand 6, silt 5, clay 4, and water 3.

In FIG. 7, 7.1 the textual and digital data. FIG. 7, 7.2 the information is presented in the Lithological column. The Other Drilling and Gas logging parameters are presented in graphical form as curves FIG. 7, 7.3.

DETAILED DESCRIPTION

Figure 1:
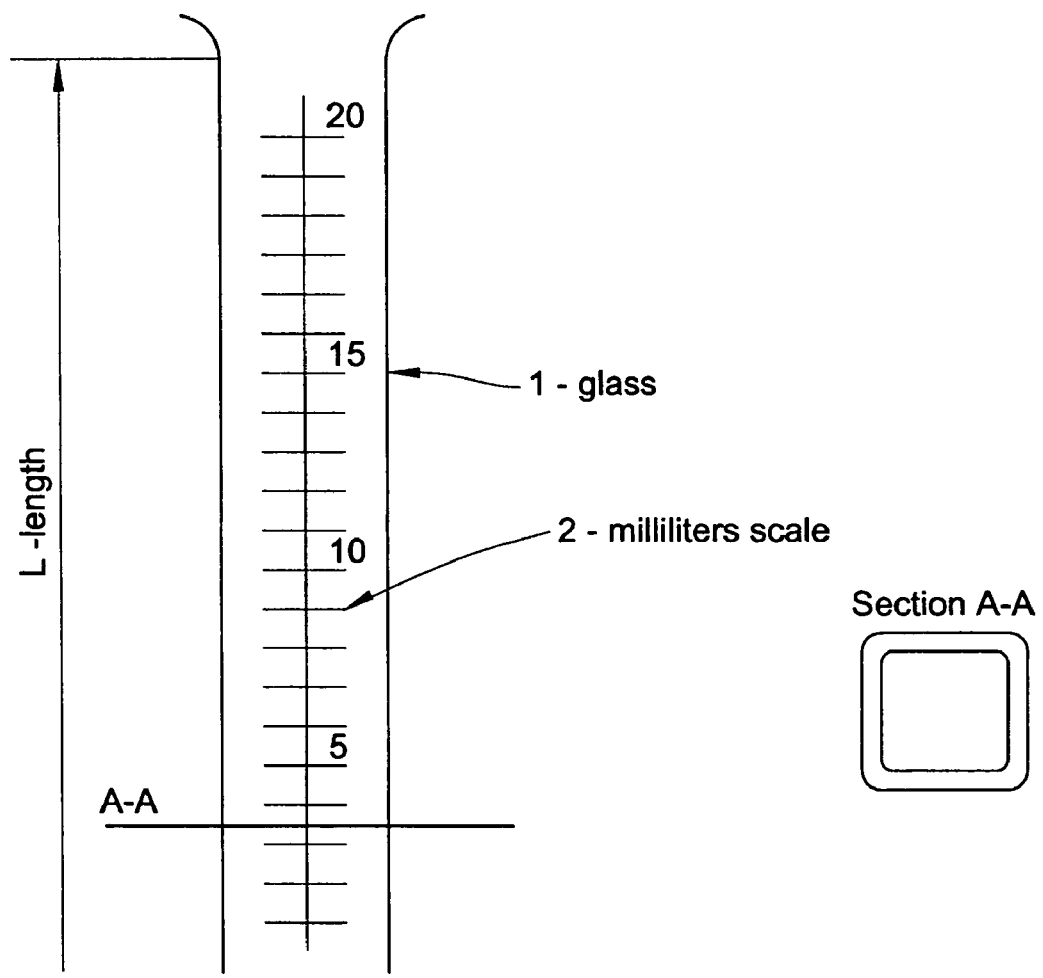
FIG. 1 is presenting a general view of a glass tube 1, which has a rectangular cross section A-A. This is a micro tube with milliliter scale 2. A small quantity of sample and water can be placed inside.
Figure 2:
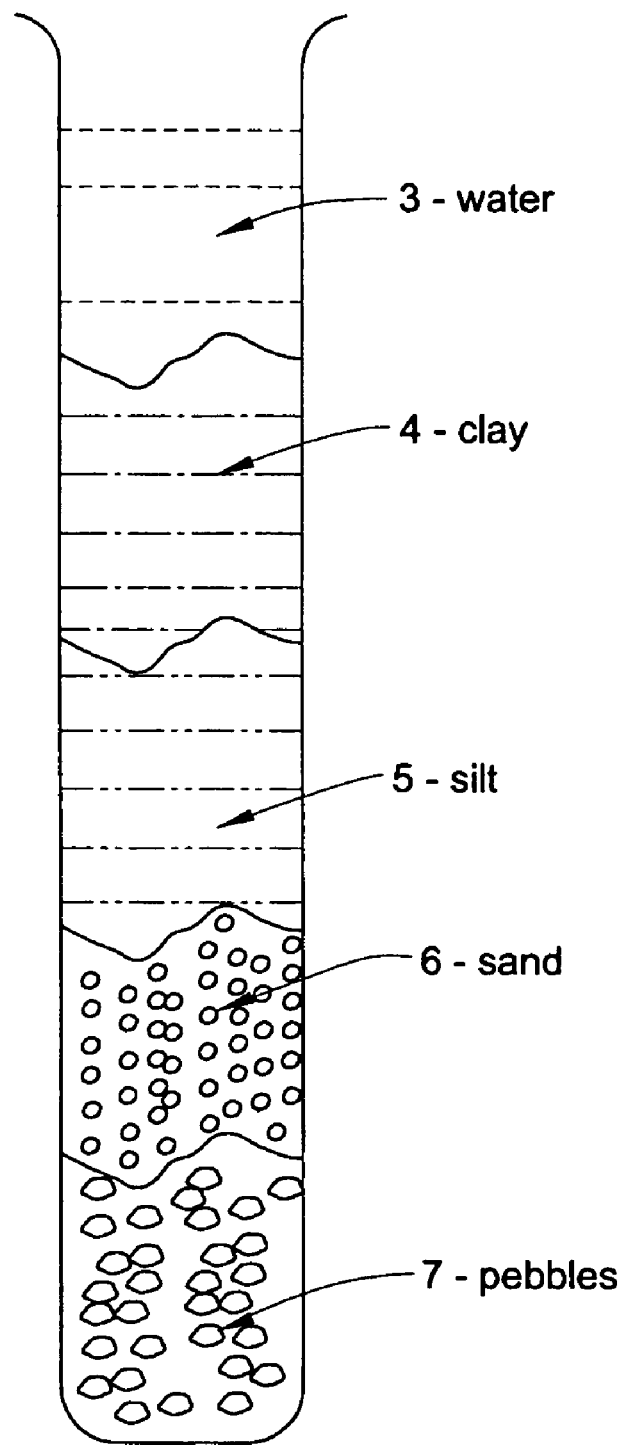
FIG. 2 is presenting a side view of micro tube with prepared sample after shaking.
Figure 3:
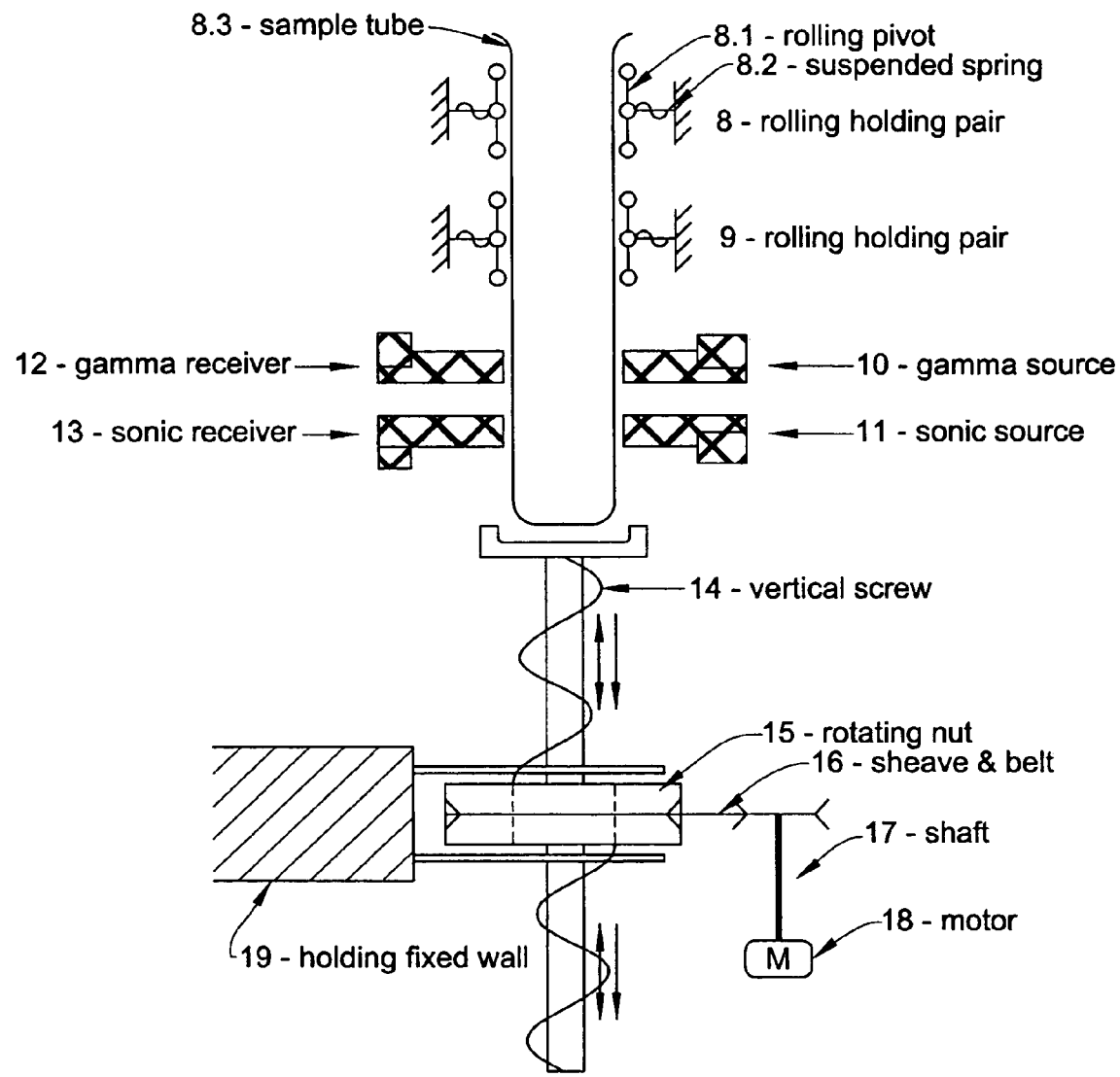
FIG. 3 is presenting general view of apparatus. The tube 8.3 slides in rolling holders 8 and 9. The rolling holders consist of rolling pivot 8.1 and are suspended by spring 8.2. The gamma source and holder 10 are placed in sliding contact with the sample tube 8.3. The sonic source 11 is on the same side as the gamma source. The gamma receiver 12 is placed opposite the source to receive the unabsorbed gamma rays. The sonic receiver 13 is placed opposite the sonic source and receives the sonic signal. The vertical screw 14 controls the precise position of tube 8.3 relative to sensors 12, 13 and sources 10, and 11. The rotating nut 15 is turned by means of sheave 16 on shaft 17, which is brought in motion by motor 18.
Figure 4:
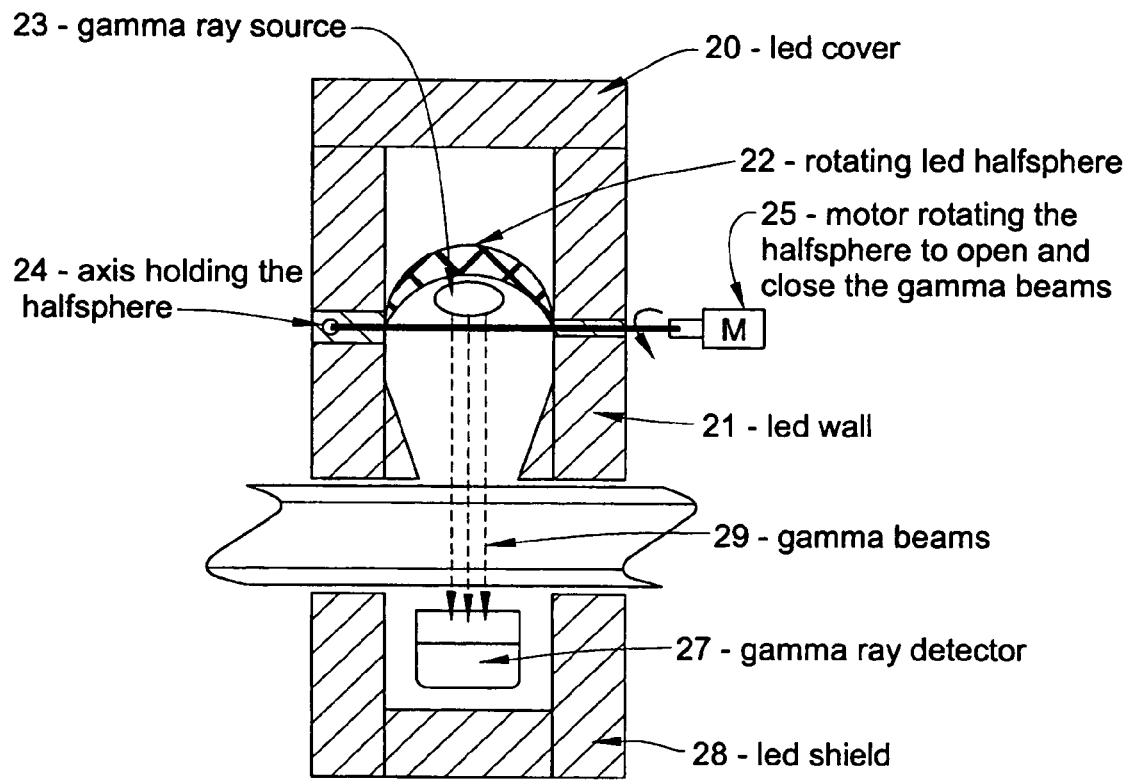
FIG. 4 is presenting miniature tube 28, which is made from lead and will absorb most of the naturally occurring background gamma rays. The pulsing source is comprised of motor 25 and axis 24 that rotates sphere 22 and it is comprised of a lead cover 20 and lead wall 21, which shield the gamma ray source 23. 27 is gamma ray detector. 29 are gamma beams.

The proposed micro granulometry apparatus and process is capable of producing detailed results with very small quantities of cuttings. This micro sample is placed in micro tube 1 and water is added. Then the aggregate is shaken and placed vertically in the Microgranulometry apparatus FIG. 3 for further analyses where the micro tube is passed along one or more sensors 10, 11, 12, 13 and the results are recorded on the computer. Quarter inch lead shielding adequately blocks the background radiation noise, so that transient gamma radiation can be measured with enough resolution for distinguishing between sand, silt and shale. Good results been achieved in the field testing of the apparatus and process disclosed by the author in U.S. Pat. No. 6,386,026, Sample Catcher and Methods of applications and U.S. Provisional Application No. 60/481,381, Drilling Cutting Analyzer System and methods of applications, also by the author.

Figure 5:
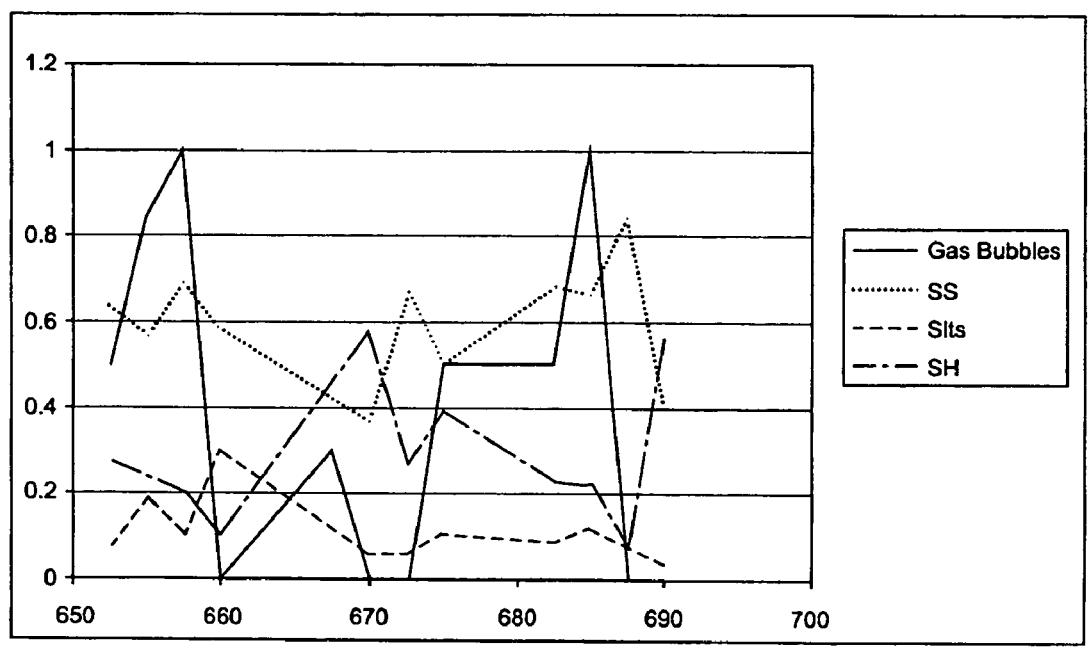
FIG. 5 is presenting the data table that shows the columns 5.1—Depth of the interval analyzed with Microgranulometry, 5.2—Gas bubbles concentration in the test tube, 5.3—Sand quantity in millimeters, 5.4—Silt quantity in millimeters, 5.5—shael/clay quantities in millimeters.
Figure 6:
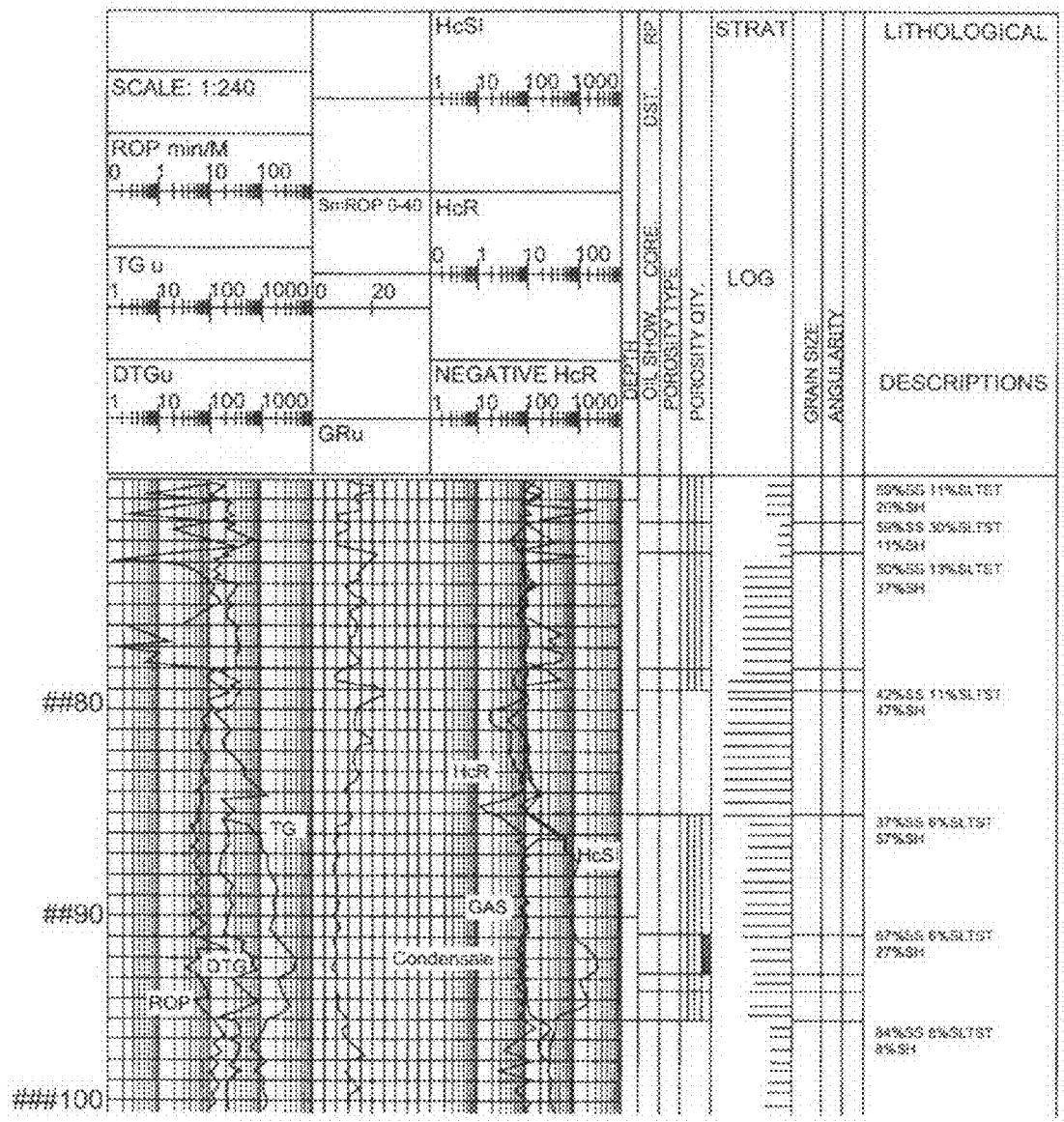
FIG. 6 is presenting the results of Microgranulometry compiled in the Geological and Geophysical Log. On this log the Microgranulometry data are graphically presented.
Figure 7:
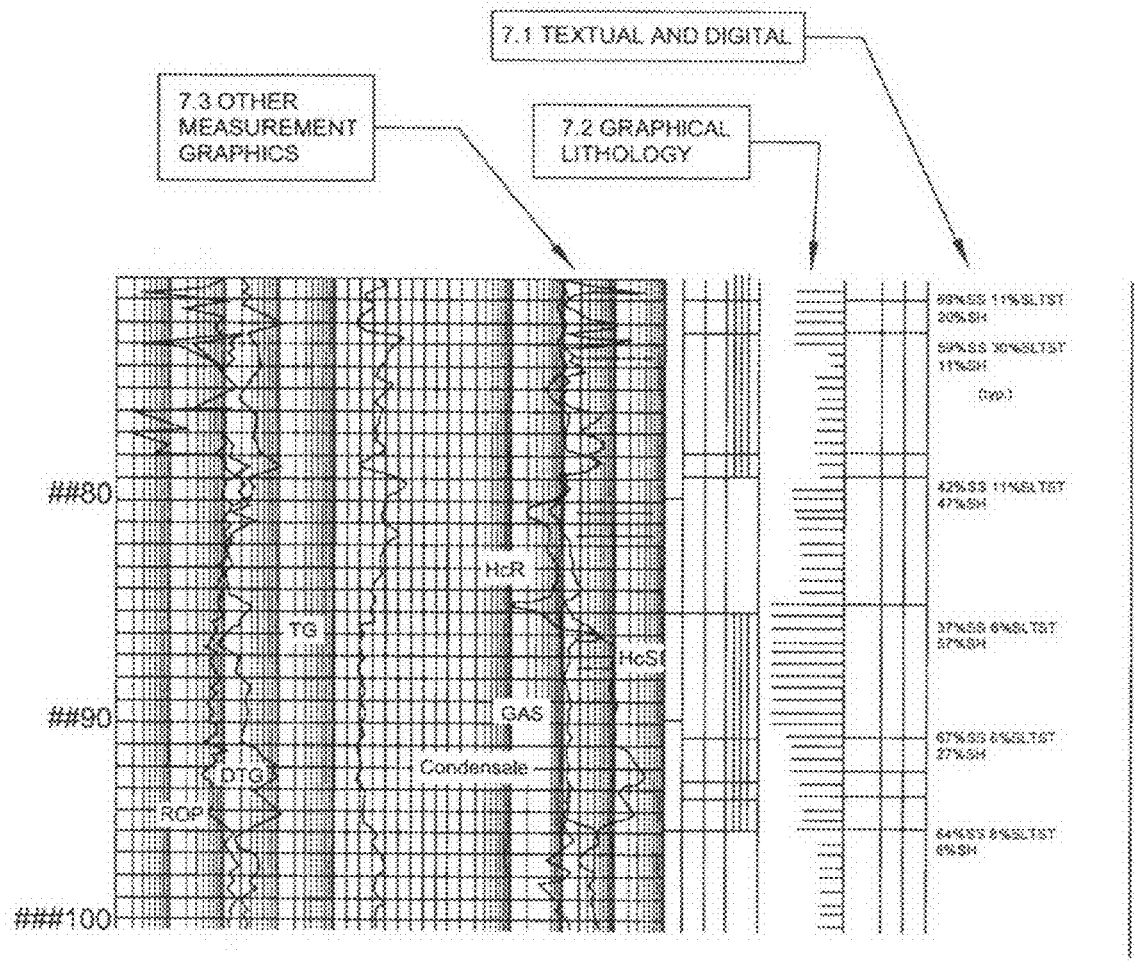
FIG. 7 is presenting the full log.

A microscopic analysis is performed by placing the micro tube 1 in front of the Horizontal microscope disclosed in U.S. Patent Provisional Application No. 60/481,408, EFS ID 48139, Horizontal Binocular Microscope for vertically gravitated and floating samples. This process allows a technician to visually distinguish the horizontal borders between the layers of Sand at the bottom, Silt in the middle and Shale/Clays on the top. The variety of sizes of sand, from coarse to very fine, is easily recognizable under the horizontal binocular microscope making detailed and efficient description possible. The transition zone between the very fine sand and silt in aggregated sample is unrecognizable in conventional sample description. In Microgranulometry the very fine sand will float down faster than the silt. This is due to the sample being ground in a mortar and pestle during preparation. Thus the silt settles on top of the very fine sand. This makes the silt clearly definable and quantitatively measurable. Similarly the aggregated components of the sample are liberated during the sample preparation and separated by the Microgranulometry procedure revealing clearly definable layers. In the case of a calcareous cemented formation the sample can be washed with acid to dissolve the calcareous cement. The difference of volume (the observed height of the substance in the test tube) before and after washing yields a quantitative measure of calcareous cement. The Bentonite (and other clays that increase in volume when hydrated) component of the sample can be quantitatively defined by the increase in volume of the contents of the test tube. This can be directly observed by the increase in height above the initial level in the test tube. In some cases the colloidal substance or hydrocarbons maybe visually distinguished. Heavy minerals will be clearly deposited at the bottom of the test tube. The microscopic observation under the horizontal microscope is very clear and detailed due to the optical properties of water. Gas bubbles may be observed on the walls of the test tubes and on the cuttings if the formation is gas bearing or overpressure gas is present in sample particles. Liquid hydrocarbons can be observed on the top of the water by using fluorescent properties of hydrocarbons. Here, UV light is used to induce fluorescence. A Measuring Scale is used to measure the vertical length of each substance in millimeters from the bottom of the test tube after the contents have settled. For example, 35 mm, 5 mm and 10 mm measurements taken in a 50 mm high sample would be recorded as the ratios 35/50, 5/50, and 10/50. The results of Microgranulometry are compiled in the Geological and Geophysical Log FIG. 6. On this log the Microgranulometry data are graphically presented FIG. 7, 7.1. The Textual and digital information is presented in the Lithological column FIG. 7, 7.2. The Other Drilling and Gas logging parameters are presented in graphical form as curves FIG. 7, 7.3. The Petro-physical calculations maybe performed in Table format with Graphical correlations analyses FIG. 5. The Data table presented in FIG. 5 shows the columns 5.1—Depth of the interval analyses with Microgranulometry, 5.2—Gas bubbles concentration in the test tube, 5.3—Sand quantity in millimeters, 5.4—Silt quantity in millimeters, 5.5—shael/clay quantities in millimeters.

Additionally, these results may be used in calculating the Environmental Index of energy of accumulation and for quantifying the Relative Permeability disclosed by the author in U.S. Pat. No. 6,301,953 B1, Date Oct. 16, 2001, Quantification of drilling mud cuttings characteristics as a measure of relative permeability.

After the analyses the micro tube 1 may be stored away for further review.

I claim:

1. Apparatus for measuring microgranulometry comprising:
   a) a micro tube (1), adapted to receive a sample in which the length is many times greater than the width and the cross-section is rectangular or circular;
   b) rolling holders (8) having rolling pivots (8.1) biased towards the micro tube (1) with spring (8.2);
   c) a gamma source (10), and a sonic source (11);
   d) a gamma receiver (12), and a sonic receiver (13); and
   e) a vertical screw (14) and rotating nut (15) for controlling the position of the micro tube (1), and thus the sample, relative to the gamma receiver (12), sonic receiver (13), gamma source (10), or sonic source (11).

2. The apparatus of claim 1, the rolling pivots (8.1) held on an axis with spring (8.2) adapted to keep the tube in a substantially vertical position and allow relative movement while maintaining proximity with the gamma receiver (12), sonic receiver (13), gamma source (10), or sonic source (11).

3. The apparatus of claim 1, the micro tube (1) having a generally rectangular cross section.

4. The apparatus of claim 3, the micro tube (1) made from glass or other transparent materials allowing further microscopic description and analysis.

5. The apparatus of claim 3, the micro tube (1) measuring 12.5 millimeters by 150 millimeters, having a total volume of 18.4 ml.

6. The apparatus of claim 1, the rolling holders comprising a pair of micro wheels made from rubber or plastic and connected with each other by a bar with rolling pivot (8.1).

7. The apparatus of claim 6, the rolling pivot (8.1) having an arm with the suspended spring pushing the micro wheels to the micro tube to hold the micro tube in a substantially vertical position.

8. The apparatus of claim 1, the gamma source (10) adapted to provide a pulsing source of directional gamma rays focused into a narrow beam.

9. The apparatus of claim 8, the pulsing source comprising a motor (25) and axis (24) adapted to rotate a sphere (22).

10. The apparatus of claim 1, the gamma receiver (12) comprising a detector, placed at the end of a tubular lead shield, adapted to detect only the gamma rays that are not absorbed by the sample in the micro tube.

11. The apparatus of claim 10, the miniature tube (28) made from lead and adapted to absorb most of the naturally occurring background gamma rays.

12. A method for measuring microgranulmetry of a sample comprising gravitationally separable particles in a micro tube, comprising:
   a) placing the sample in the micro tube;
   b) agitating the sample with water in the micro tube;
   c) measuring distinguishing properties of the gravitationally separable particles of the sample, as data;
   d) recording and interpreting the data; and
   e) performing microscopic examination of the sample as a layered aggregate.

13. The method of claim 12, the step of placing the sample in the micro tube comprising extracting a relatively small sample from a main bulk sample and dispersing the small sample in a dry condition into the micro tube (1).

14. The method of claim 12, the step of agitating a mixture of the sample with water in the micro tube comprising adding water to the micro tube with the sample and closing the top of the micro tube with a cap, and then shaking the micro tube until the sample becomes mixed in the water.

15. The method of claim 12, the step of measuring the distinguishing properties of the gravitationally separable particles of the sample in the micro tube includes a means for passing the micro tube in close proximity to sources (10), (11) and corresponding sensors (12), (13) so as to obtain a useful signal on an electronic measuring device.

16. The method of claim 12, the step of recording and interpreting the data comprising using software that is capable of further processing the data for interpretation.

17. The method of claim 12, the step of performing microscopic examination of the sample as a layered aggregate comprising viewing the side of the micro tube to describe and measure the layers in the micro tube based on its visual characteristics.

18. The method of claim 12, the distinguishing properties comprising grain size.

19. The method of claim 12, the distinguishing properties comprising substance.

20. The method of claim 12, the distinguishing properties comprising the ratio of one group of gravitationally separable particles to another group of gravitationally separable particles.

* * * * *